United States Patent
Fry et al.

(10) Patent No.: US 10,458,909 B1
(45) Date of Patent: Oct. 29, 2019

(54) MEMS OPTICAL SENSOR

(71) Applicant: INTERNATIONAL BUSINESS MACHINES CORPORATION, Armonk, NY (US)

(72) Inventors: Jonathan Fry, Fishkill, NY (US); Daniel Piper, Vancouver, WA (US); Jang Sim, Hopewell Junction, NY (US); Yongchun Xin, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/170,013

(22) Filed: Oct. 24, 2018

(51) Int. Cl.
  *G01N 21/41* (2006.01)
  *B01L 3/00* (2006.01)
  *G02B 6/122* (2006.01)

(52) U.S. Cl.
  CPC .... *G01N 21/4133* (2013.01); *B01L 3/502715* (2013.01); *G02B 6/122* (2013.01); *B01L 2300/0627* (2013.01); *B01L 2300/08* (2013.01)

(58) Field of Classification Search
  CPC ... G01N 2015/1493; G01N 2015/1497; G01N 21/31; G01N 35/08; G01N 15/1427; G01N 15/1429; G01N 15/1475; G01N 1/14; G01N 2015/1075; G01N 2015/1087; G01N 2015/144; G01N 2015/1445; G01N 2015/1452; G01N 2015/1472; G01N 2015/1477; G01N 21/51; G01N 21/8851; G01N 21/9027; G01N 27/44743; G01N 27/44769; G01N 15/1463; G01N 21/05; G01N 21/4133; G01N 2201/06113; G01N 2201/068; G01N 2201/12; G01N 30/02; G01N 30/32; G01N 15/1459; G01N 2030/027; G01N 2030/085; G01N 2030/328; G01N 21/33; G01N 21/41; G01N 21/53; G01N 21/553; G01N 21/6452; G01N 21/6454; G01N 21/6458; G01N 21/648;
(Continued)

(56) References Cited

U.S. PATENT DOCUMENTS 5,305,071 A 4/1994 Wyatt
5,377,008 A 12/1994 Ridgway et al.
(Continued)

FOREIGN PATENT DOCUMENTS

TW 504491 B 10/2002

*Primary Examiner* — Michael P Stafira
(74) *Attorney, Agent, or Firm* — Law Offices of Ira D. Blecker, P.C.

(57) ABSTRACT

A micro electrical mechanical system (MEMS) optical sensor including a fluid channel having an input portion, an output portion and a curved portion positioned between the input portion and the output portion; a light source impinging on a first boundary of the curved portion and exiting from a second boundary of the curved channel; a photodetector to record a light path of refraction of the light source exiting from the second boundary of the curved portion; a processor to compute the refractive index of a fluid in the curved portion using the light path of refraction of the light source and compare the computed refractive index to a known refractive index for the fluid to determine a difference between the computed refractive index and the known refractive index.

20 Claims, 4 Drawing Sheets

(58) Field of Classification Search
CPC .......... G01N 2201/0636; G01N 30/20; G01N 30/88; G01N 15/0211; G01N 15/1404; G01N 15/1434; G01N 15/1436; G01N 15/1484; G01N 1/4055; G01N 2001/4061; G01N 2015/1006; G01N 2015/1415; G01N 2021/058; G01N 2021/154; G01N 2021/1731; G01N 2021/3181; G01N 2030/009; G01N 2030/143; G01N 2030/201; G01N 2030/202; G01N 2030/324; G01N 2030/326; G01N 2030/347; G01N 2030/528; G01N 2030/8804; G01N 2030/8854; G01N 2030/889; G01N 2035/0444; G01N 21/0303; G01N 21/0332; G01N 21/15; G01N 21/274; G01N 21/43; G01N 21/55; G01N 21/554; G01N 21/6428; G01N 21/6486; G01N 21/7743; G01N 21/85; G01N 2201/1211; G01N 30/04; G01N 30/08; G01N 30/14; G01N 30/26; G01N 30/34; G01N 30/461; G01N 30/468; G01N 30/52; G01N 30/6052; G01N 30/64; G01N 30/74; G01N 30/8675; G01N 30/8696; G01N 30/95; G01N 33/182; G01N 33/2823; G01N 33/2835; G01N 33/557; G01N 35/1097; G02B 2027/0178; G02B 27/0172; G02B 5/0816; G02B 5/0841; G02B 5/26; G02B 5/281; G02B 5/285; G02B 5/3041; G02B 1/11; G02B 1/14; G02B 2006/12069; G02B 2006/121; G02B 2006/12138; G02B 2027/011; G02B 2027/0138; G02B 2027/014; G02B 26/0841; G02B 27/0093; G02B 27/141; G02B 5/0242; G02B 5/0247; G02B 5/208; G02B 5/223; G02B 5/282; G02B 5/283; G02B 5/287; G02B 5/3083; G02B 5/32; G02B 6/02076; G02B 6/1221; G02B 6/1223; G02B 6/1228; G02B 6/138; G02B 6/262; G02B 6/32; G02B 6/4202; G02B 6/43; G01B 11/16; G01B 13/12; G01J 1/429; G01J 2003/1213; G01J 2003/2866; G01J 3/00; G01J 3/0208; G01J 3/021; G01J 3/0218; G01J 3/0262; G01J 3/0286; G01J 3/0291; G01J 3/04; G01J 3/10; G01J 3/18; G01J 3/28; G01J 3/2803; G01J 3/42

See application file for complete search history.

(56) References Cited

U.S. PATENT DOCUMENTS

| | | | |
|---|---|---|---|
| 7,386,199 B2 | 6/2008 | Schmidt et al. | |
| 7,477,384 B2 | 1/2009 | Schwabe | |
| 7,502,109 B2 | 3/2009 | Bonne et al. | |
| 8,111,401 B2 | 2/2012 | Magnusson et al. | |
| 8,441,645 B2 | 5/2013 | Prabhakar et al. | |
| 8,537,353 B2 | 9/2013 | Liu et al. | |
| 8,542,353 B2 | 9/2013 | Christian et al. | |
| 2008/0030693 A1* | 2/2008 | Kim | G01N 21/4133 355/18 |
| 2012/0069328 A1* | 3/2012 | Wootten | G01N 21/431 356/133 |
| 2012/0170044 A1* | 7/2012 | Prabhakar | G01N 21/05 356/440 |
| 2013/0057863 A1* | 3/2013 | Christiansen | G01N 21/0303 356/409 |
| 2014/0177932 A1* | 6/2014 | Milne | G01N 21/9027 382/128 |
| 2016/0305937 A1 | 10/2016 | Steinmiller et al. | |
| 2019/0079543 A1* | 3/2019 | Tincher | B01F 5/043 |

\* cited by examiner

MEMS OPTICAL SENSOR

BACKGROUND

The present exemplary embodiments pertain to optical sensors and, more particularly, to optical sensors in Micro Electrical Mechanical System (MEMS) application.

Micro electrical mechanical system (MEMS) is the technology of microscopic devices and is particularly concerned with devices having moving parts. In some cases, MEMS devices are used in the dispensation of chemicals especially where the dispensation is at the micro scale and the amounts of the chemicals need to be dispensed in exact amounts. In such cases, the MEMS devices need to be able to control a volume of each dispensed chemical and it is often required that this volumetric control system be robust and able to withstand motion and movement.

MEMS applications may have channels for the flow of fluids. The fluid in a certain channel may change or switch for a certain purpose. Accordingly, it is necessary to characterize the fluid in the channel since the quality of the fluid may degrade or change as based on the MEMS functions.

BRIEF SUMMARY

The various advantages and purposes of the exemplary embodiments as described above and hereafter are achieved by providing, according to an aspect of the exemplary embodiments, a micro electrical mechanical system (MEMS) optical sensor comprising: a fluid channel having an input portion, an output portion and a curved portion positioned between the input portion and the output portion; a light source impinging on a first boundary of the curved portion and exiting from a second boundary of the curved channel; a photodetector to record a light path of refraction of the light source exiting from the second boundary of the curved portion; a processor to compute the refractive index of a fluid in the curved portion using the light path of refraction of the light source and compare the computed refractive index to a known refractive index for the fluid to determine a difference between the computed refractive index and the known refractive index.

According to another aspect of the exemplary embodiments, there is provided a micro electrical mechanical system (MEMS) comprising: a fluid channel having an input portion, an output portion and a curved portion positioned between the input portion and the output portion; an optical sensor comprising: a light source impinging on a first boundary of the curved portion and exiting from a second boundary of the curved channel; a photodetector to record a light path of refraction of the light source exiting from the second boundary of the curved portion; a processor to compute the refractive index of a fluid in the curved portion using the light path of refraction of the light source and compare the computed refractive index to a known refractive index for the fluid to determine a difference between the computed refractive index and the known refractive index.

According to a further aspect of the exemplary embodiments, there is provided a method of optically sensing a fluid in a micro electrical mechanical system (MEMS) comprising: forming a fluid channel in a substrate having an input portion, an output portion and a curved portion positioned between the input portion and the output portion; impinging a light source on a first boundary of the curved portion and exiting the light source from a second boundary of the curved channel; recording by a photodetector light path of refraction of the light source exiting from the second boundary of the curved portion; computing by a processor the refractive index of a fluid in the curved portion using the light path of refraction of the light source and comparing by the processor the computed refractive index to a known refractive index for the fluid to determine a difference between the computed refractive index and the known refractive index.

BRIEF DESCRIPTION OF SEVERAL VIEWS OF THE DRAWINGS

The features of the exemplary embodiments believed to be novel and the elements characteristic of the exemplary embodiments are set forth with particularity in the appended claims. The Figures are for illustration purposes only and are not drawn to scale. The exemplary embodiments, both as to organization and method of operation, may best be understood by reference to the detailed description which follows taken in conjunction with the accompanying drawings in which:

DETAILED DESCRIPTION

The present inventors have proposed a MEMS optical sensor that can quickly characterize fluids in a channel.

It is proposed to incorporate one or a plurality of MEMS optical sensors into a microfluidics system, with no moving parts and instant feedback. These sensors may be used for MEMS pump feedback control and exact dispensing systems as pump characteristics may change over time or liquids may change due to different targets.

It is within the scope of the exemplary embodiments to gang the MEMS optical sensors together to quantize/control larger doses and multiple kinds of liquids.

Figure 1:
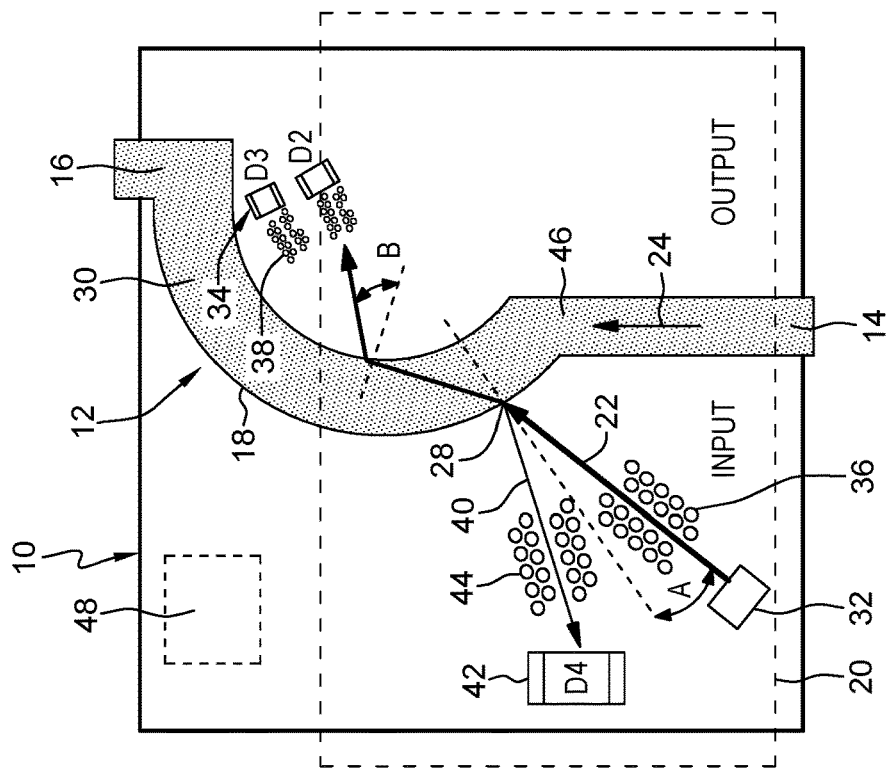
FIG. 1 is an illustration of a substrate having a fluid channel without fluid and a MEMS optical sensor.

Referring to the Figures in more detail, and particularly referring to FIG. 1, there is illustrated a substrate 10 having a fluid channel, generally indicated by 12. The substrate 10 may be, for example, silicon. In one exemplary embodiment, the substrate 10 may be formed on a semiconductor device.

The fluid channel includes an input portion 14, an output portion 16 and a curved portion 18. The importance of the curved portion will be discussed below.

Located on or incorporated within substrate 10 is a MEMS optical sensor 20. The MEMS optical sensor 20 may work by refractometry. An incident light 22 is impinged on the curved portion 18 of the channel 12, passes through the curved portion 18 of the channel 12 and exits from the curved portion 18 of the channel 12. The path of the light beam 22 bends as the light beam 22 progresses through the substrate 10, through the curved portion 18 of the channel 12 and back into the substrate 10 as the substrate 10 and channel 12 have different indices of refraction. The bending of the light beam 22 in the channel 18 is characteristic of the fluid in the channel 12. As shown in FIG. 1, there is no fluid in the channel 12. If there was a fluid in the channel 18, it would flow in the direction indicated by the arrow 24. The actual direction of flow of the fluid has no effect on the refractometry as practiced in the exemplary embodiments.

Figure 3:
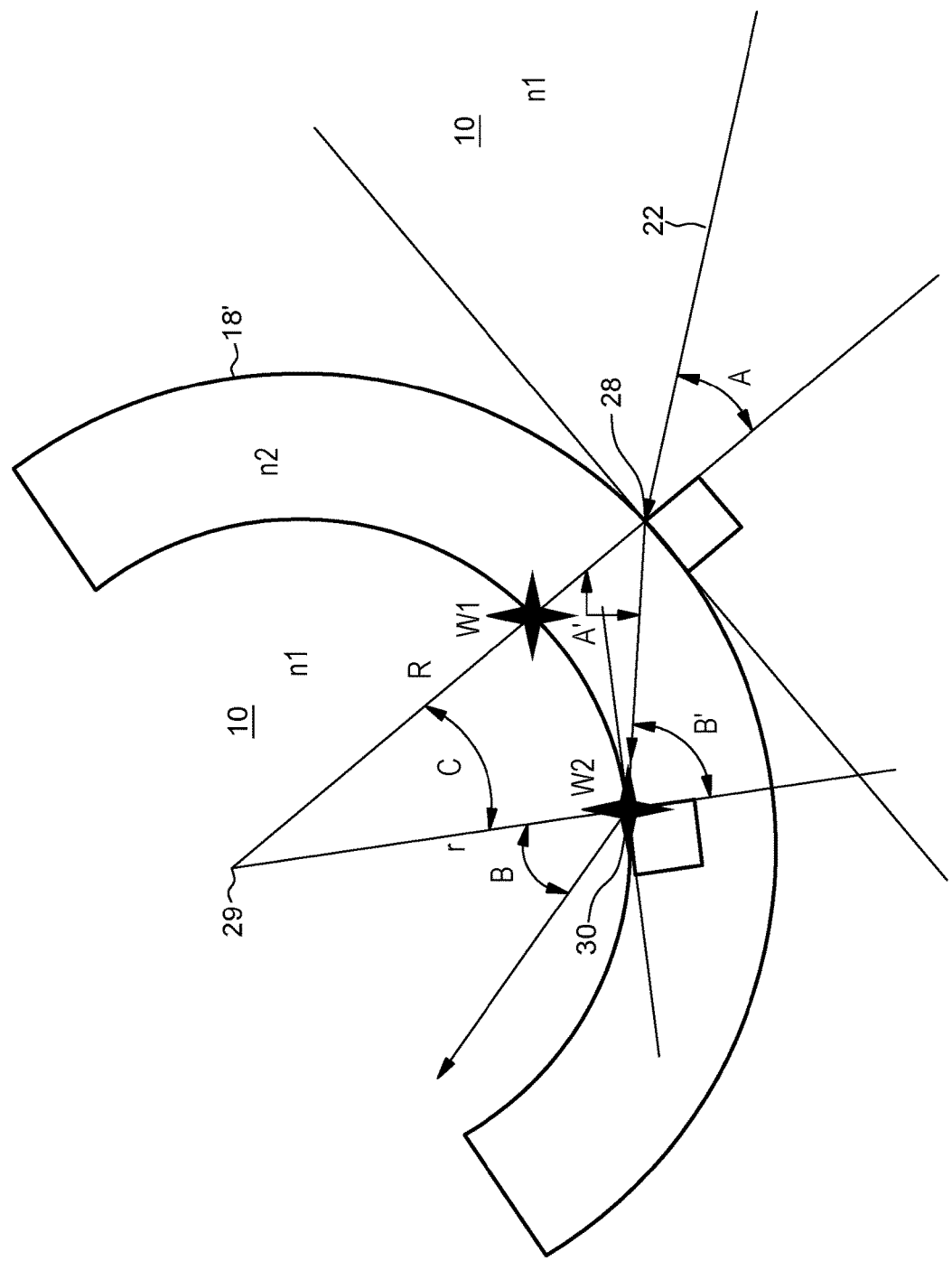
FIG. 3 is an illustration of an exaggerated curved portion of the fluid channel of the substrate of FIG. 1.

Referring now to FIG. 3, there is illustrated an exaggerated curved portion 18' of the fluid channel 12 to demonstrate the importance of the curved portion 18 of the channel 12. The incident light 22 impinges on a first boundary 28 of the curved portion 18'. The light 22 passes through the curved portion 18' and exits at the second boundary 30 of the curved portion 18'. The substrate 10 has an index of refraction n1 and the curved portion 18' has an index of refraction n2. The angle of incidence A is measured with respect to a line that is normal to the first boundary 28 of the curved portion 18. The output angle B is measured with respect to a line that is normal to the second boundary 30 of the curved portion 18'. The light shift from W1 to W2 can be used to determine the index of refraction n1. It can be demonstrated that the double curved interface of the curved portion will enhance the output angle B and the light path output point shift of W1 to W2, both of which improve the accuracy of the index of refraction determination than would a straight channel.

The curved portion 18' shown in FIG. 3 has a shape in the form of a segment of a circle for the purpose of illustration and not limitation.

The actual shape of the curved portion 18 of the channel 12 may be any spherical arc, elliptical arc, parabolic arc or other similarly defined conic section. It may also be segmented/approximated (e.g. stop-sign octagon). It may also be computationally or approximately defined (e.g. complex polynomial expansion, inverse polynomial, etc.), using methods similar to those to specify lens curvature for optics.

To contrast with a "straight" segment, the curve adds the capability of predictably changing the second incident angle B', from fluid back into the substrate 10, to promote higher resolution of refractive index detection via elongation of the input output swept-curve distance, as well as enabling out of range detection for the case of total internal reflection at the second boundary 30.

For the purpose of illustration and not limitation, given present day lithography limitations, the channel width may be 10 to 100 μm. A present day sensor array size may be down to 100 nm. It is assumed that the minimum inner radius "r" of the circle segment in FIG. 3 is 50 μm and channel width is 10 um. Accordingly, the minimum outer radius "R" of the circle segment in FIG. 3 is 60 μm. Including substrate boundary, the minimum size of device with the curved portion 18' in FIG. 3 is 0.14*0.08=0.0112 mm². For such a sensor array, with these dimensions, the minimum arc between sensors to obtain W1 and W2 is 0.11 degrees. From calculation based on a silicon based curved portion device as described above and a designed inject angle A of 13° in FIG. 3, a detection resolution of refractive index is 0.01 and detection range of refractive index is as wide as from 1 to 2.

Referring back to FIG. 1, the angle of incidence A and output angle B are measured in the same way as in FIG. 3. The light 22 may be provided by a light source 32 having good directional travel which may be, for example, a laser or if not a laser, then a light source using a single mode wave guide to align the light source 32. If substrate 10 is on a semiconductor device, the light source 32 may be integrated with the semiconductor device.

The light 22 exiting from the curved portion 18 may be detected by one of the ganged detectors 34, for example, detector D3 shown in FIG. 1. The detectors 34 may be, for example, photodiodes and may be integrated with the underlying semiconductor device if present.

Preferably, the MEMS optical sensor 20 may further include waveguides 36, 38, respectively, to guide the light 22 from the light source 32 to the curved portion 18 and from the curved portion 18 to the detectors 34. Optical waveguides 36, 38 may be planar, strip, or fiber waveguides, single- or multi-mode and made from, for example, glass, polymer or semiconductor materials. The optical waveguides 36, 38 may be, for example, optical fibers.

The angle of incidence A is held constant during any period of testing. From time to time the angle of incidence A may be verified by measuring the reflected light 40 into detector 42. Waveguides 44 are preferred to guide the light 40 into detector 42.

The detectors 34 enable the measuring of the output angle B and output location of the light path.

Figure 2:
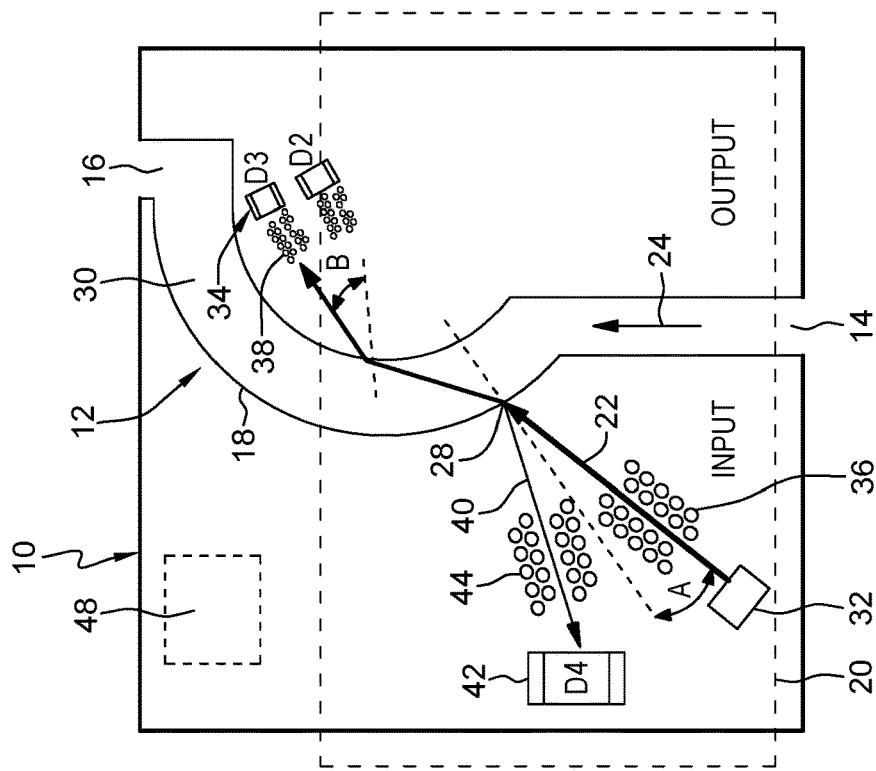
FIG. 2 is an illustration of the substrate and MEMS optical sensor of FIG. 1 with a fluid in the fluid channel.

Referring now to FIG. 2, fluid 46 has now entered the channel 12 flowing in the direction of arrow 24. The angle of incidence A remains the same but the output light path has shifted due to the different index of refraction of fluid 46. The refracted light has now been detected by detector D2. The output angle B is not changed if the curved portion 18 is a perfect circle. The output light path is shown as the shift from W1 to W2 in FIG. 3.

The calculation of the index of refraction n2 may best be handled by processor 48 from the underlying semiconductor device for example. It is preferred that the curved portion 18 of the channel 12 be in the form of an arc of a circle as the calculation of the index of refraction n2 is straight forward as described below.

Referring to FIG. 3, for a circle channel assume:

an inner radius r between the second boundary 30 and center 29 of the curved portion 18' and outer radius R between the first boundary 28 and the center of the circle 29 where R>r;

n1 is the refractive index of the substrate 10; and n2 is the refractive index of the fluid in the channel.

Then, $$\sin A' = \frac{n_s}{n_c} \cdot \sin A$$

$$\sin B' = \frac{n_s}{n_c} \cdot \frac{R}{r} \sin A$$

$$\angle C = \angle B' - \angle A' = \sin^{-1}\left(\frac{n_s}{n_c} \cdot \frac{R}{r} \sin A\right) - \sin^{-1}\left(\frac{n_s}{n_c} \cdot \sin A\right)$$

The arc between W1 and $$W2 = \frac{\angle C}{2\pi} r.$$

Then, when the Arc W1 to W2 is measured by the detectors 34, we have ∠C measured.

Therefor n2 can be calculated as:

$$n2 = \left[\left(\frac{R}{r}\right)^2 - 2\left(\frac{R}{r}\right)\cos C + 1\right] \cdot n_s \cdot \frac{\sin A}{\sin C}$$

When B' is right angle, the $1^{st}$ order test reach $$n2 \text{ low end limit} = n1 \cdot \frac{R}{r} \sin A$$

which makes the calculation of the index of refraction n2 simpler.

The index of refraction n2 of the curved portion 18 may be calculated from other curved configurations of the curved portion 18 but the calculations are more complex and may require mathematical functions used in optics such as computational ray tracing or a point spread function. For a non-circle channel, the channel may be designed that has Arc W1 to W2 larger than in the circle case, therefore get better resolution.

The computed index of refraction of the fluid may be compared with what the index of refraction of the fluid is supposed to be. If there is no difference, then the fluid in the channel 18 meets specifications. If there is a difference, then the composition of the fluid in the channel 18 may need to be adjusted.

Based on the need of the channel, a number of different actions may be taken. If there is no difference, as computed above, a valve may be opened to allow the fluid to flow. Or, if there is no valve, the fluid may just be monitored for changes as it passes through the channel 18. If there is a difference, as computed above, a valve may close to prevent further fluid flow. Or, a signal may be sent downstream to adjust the composition of the fluid so that the adjusted fluid will meet specifications.

Figure 4:
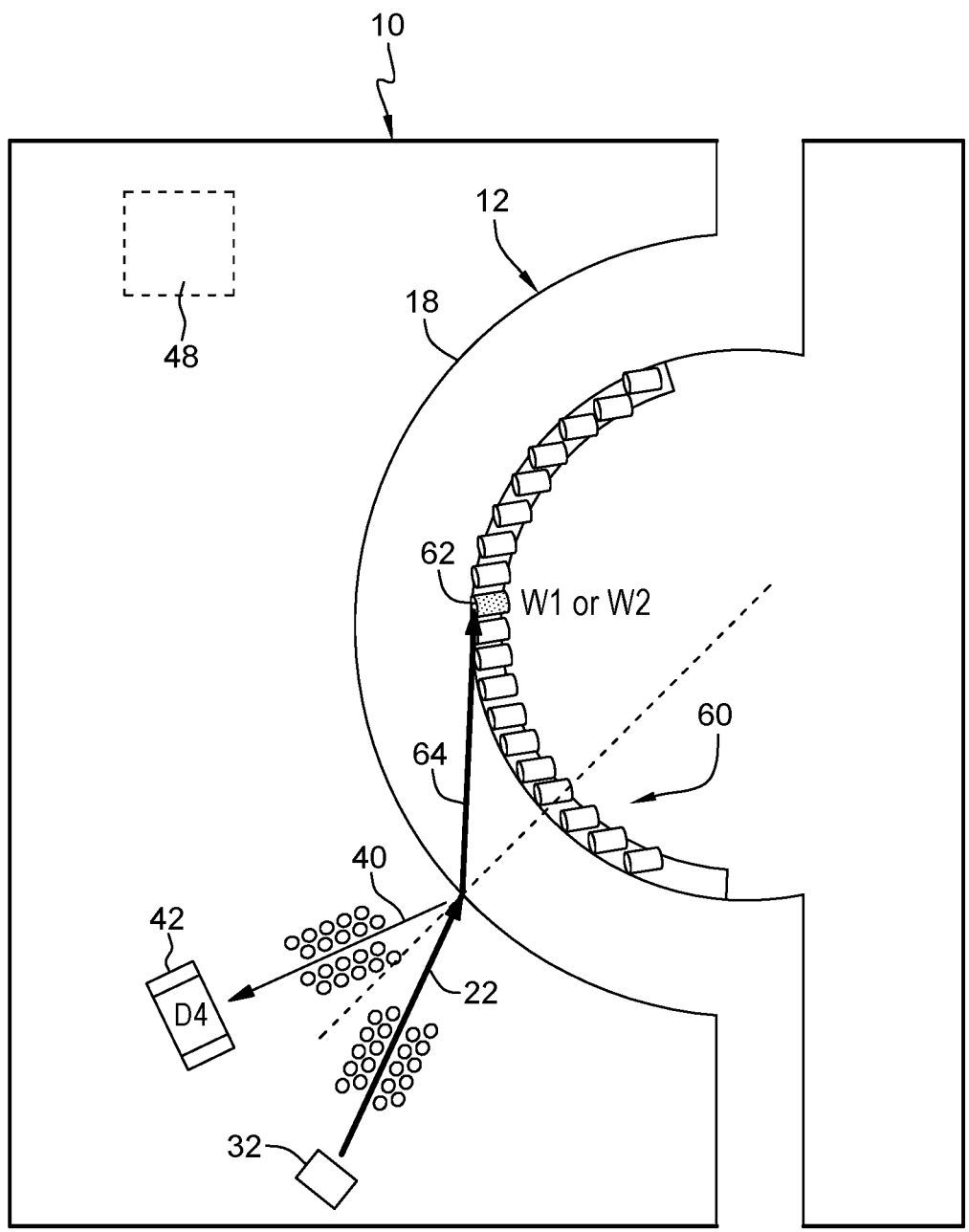
FIG. 4 is an illustration similar to that shown in FIGS. 1 and 2 but with a detector array on the outer boundary of the curved portion of the channel.

A further exemplary embodiment is illustrated in FIG. 4. This exemplary embodiment is identical to that shown in FIGS. 1 and 2 except that there is an integrated detector array 60 along the output boundary of the curved portion 18 to detect the output light path. There is no need for waveguides to guide the light to the detectors 60. In FIG. 4, the refracted light 64 is output to detector 62. It is not specified in this FIG. 4 whether the refracted light 64 is without fluid in the channel 12, in which case the detector would be at W1, or the refracted light 64 is with fluid in the channel 12, in which case the detector would be at W2.

While the previous exemplary embodiments show detectors on the inside of the arc for detecting the light path, depending on the material properties (refractive index) of both the substrate and the anticipated fluids in the channel, it is within the scope of the exemplary embodiments to have the detectors on the outside of the arc and have the incident light on the inner surface.

Figure 5:
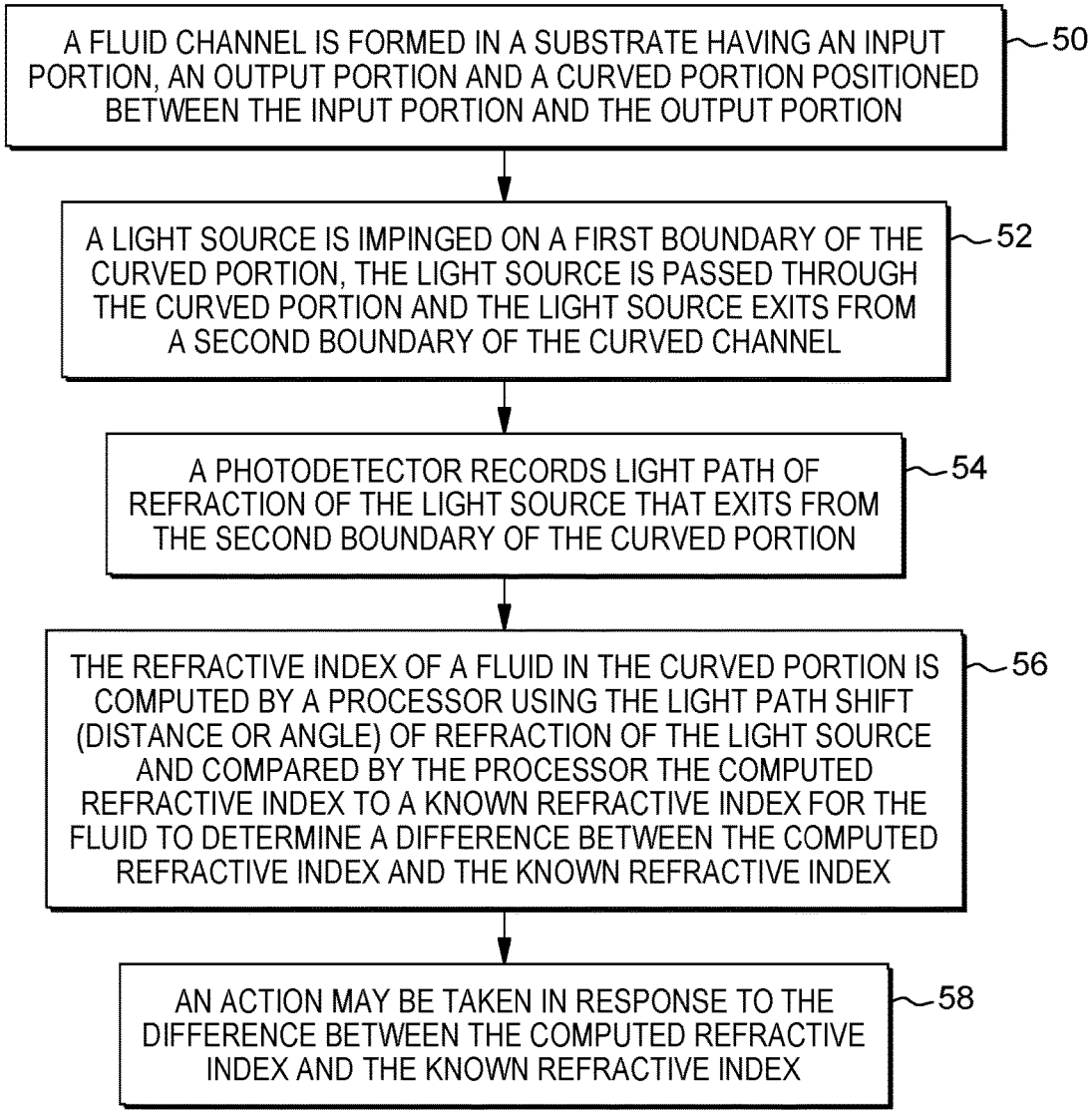
FIG. 5 is a flowchart of a method of optically sensing a fluid in a MEMS.

The exemplary embodiments may further include a method of optically sensing a fluid in a micro electrical mechanical system (MEMS) as illustrated in FIG. 5.

The method may include a fluid channel formed in a substrate having an input portion, an output portion and a curved portion positioned between the input portion and the output portion, box 50.

A light source is impinged on a first boundary of the curved portion, passing the light source through the curved portion and exiting the light source from a second boundary of the curved channel, box 52.

A photodetector records a light path of refraction of the light source exiting from the second boundary of the curved portion, box 54.

The refractive index of a fluid in the curved portion is computed by a processor using the light path shift (distance or angle) of refraction of the light source and compared by the processor the computed refractive index to a known refractive index for the fluid to determine a difference between the computed refractive index and the known refractive index, box 56.

An action may be taken in response to the difference between the computed refractive index and the known refractive index, box 58.

The substrate and MEMS optical sensor may be fabricated by conventional techniques related to semiconductor device and integrated circuit (IC) fabrication. In particular, various steps in the manufacture of semiconductor devices and semiconductor-based ICs are well known and so, in the interest of brevity, many conventional steps will only be mentioned briefly herein or will be omitted entirely without providing the well-known process details.

In general, the various processes used to form a microchip that will be packaged into an IC fall into four general categories, namely, film deposition, removal/etching, semiconductor doping and patterning/lithography. Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Removal/etching is any process that removes material from the wafer. Examples include etch processes (either wet or dry), and chemical-mechanical planarization (CMP), and the like. Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device. Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

A surface layer of silicon or silicon nitride may be formed on the semiconductor device by conventional techniques. Thereafter, the channel may be formed in the surface layer. The waveguides, light source and photodetectors may be formed in or on the surface layer. A topping layer deposited over the channel, waveguides, light source and photodetectors.

It will be apparent to those skilled in the art having regard to this disclosure that other modifications of the exemplary embodiments beyond those embodiments specifically described here may be made without departing from the spirit of the invention. Accordingly, such modifications are considered within the scope of the invention as limited solely by the appended claims.

What is claimed is:

1. A micro electrical mechanical system (MEMS) optical sensor comprising:
    a fluid channel having an input portion, an output portion and a curved portion positioned between the input portion and the output portion;

a light source impinging on a first boundary of the curved portion and exiting from a second boundary of the curved channel;

a photodetector to record a light path of refraction of the light source exiting from the second boundary of the curved portion;

a processor to compute the refractive index of a fluid in the curved portion using the light path of refraction of the light source and compare the computed refractive index to a known refractive index for the fluid to determine a difference between the computed refractive index and the known refractive index.

2. The MEMS optical sensor of claim 1 wherein the curved portion has a shape in the form of a circular arc, spherical arc, elliptical arc or parabolic arc.

3. The MEMS optical sensor of claim 1 wherein there are a plurality of photodetectors to record the light path of refraction.

4. The MEMs optical sensor of claim 3 wherein the plurality of photodetectors are on the second boundary to record the light path of refraction.

5. The MEMS optical sensor of claim 1 wherein there is an incident waveguide to guide the light source impinging on the first boundary.

6. The MEMS optical sensor of claim 5 wherein there is a refractive waveguide to guide the light source exiting from the second boundary.

7. The MEMS optical sensor of claim 1 further comprising a second photodetector to record an angle of incidence of the light source impinging on the first boundary.

8. The MEMS optical sensor of claim 1 further comprising an action taken in response to the difference between the computed refractive index and the known refractive index.

9. A micro electrical mechanical system (MEMS) comprising:

a fluid channel having an input portion, an output portion and a curved portion positioned between the input portion and the output portion;

an optical sensor comprising:

a light source impinging on a first boundary of the curved portion and exiting from a second boundary of the curved channel;

a photodetector to record a light path of refraction of the light source exiting from the second boundary of the curved portion;

a processor to compute the refractive index of a fluid in the curved portion using the light path of refraction of the light source and compare the computed refractive index to a known refractive index for the fluid to determine a difference between the computed refractive index and the known refractive index.

10. The MEMS of claim 9 wherein the curved portion has a shape in the form of a circular arc, spherical arc, elliptical arc or parabolic arc.

11. The MEMS of claim 9 wherein there are a plurality of photodetectors to record the light path of refraction.

12. The MEMS of claim 9 wherein there is an incident waveguide to guide the light source impinging on the first boundary.

13. The MEMS of claim 9 further comprising a second photodetector to record an angle of incidence of the light source impinging on the first boundary.

14. The MEMS of claim 9 further comprising an action taken in response to the difference between the computed refractive index and the known refractive index.

15. A method of optically sensing a fluid in a micro electrical mechanical system (MEMS) comprising:

forming a fluid channel in a substrate having an input portion, an output portion and a curved portion positioned between the input portion and the output portion;

impinging a light source on a first boundary of the curved portion and exiting the light source from a second boundary of the curved channel;

recording by a photodetector light path of refraction of the light source exiting from the second boundary of the curved portion;

computing by a processor the refractive index of a fluid in the curved portion using the light path of refraction of the light source and comparing by the processor the computed refractive index to a known refractive index for the fluid to determine a difference between the computed refractive index and the known refractive index.

16. The method of optically sensing a fluid in a MEMS of claim 15 wherein the curved portion has a shape in the form of a circular arc, spherical arc, elliptical arc or parabolic arc.

17. The method of optically sensing a fluid in a MEMS of claim 16 wherein recording by a photodetector further includes recording by a plurality of photodetectors to record the light path of refraction.

18. The method of optically sensing a fluid in a MEMS of claim 16 further comprising guiding by an incident waveguide the light source impinging on the first boundary.

19. The method of optically sensing a fluid in a MEMS of claim 16 further comprising recording by a second photodetector an angle of incidence of the light source impinging on the first boundary.

20. The method of optically sensing a fluid in a MEMS of claim 16 further comprising taking an action in response to the difference between the computed refractive index and the known refractive index.

* * * * *